(12) United States Patent
Wilken

(10) Patent No.: US 7,721,566 B1
(45) Date of Patent: May 25, 2010

(54) COLLAPSIBLE INTERCONNECTED PANELS OF PHASE CHANGE MATERIAL

(75) Inventor: Kenneth Wilken, Plymouth, MN (US)

(73) Assignee: Minnesota Thermal Science, LLC, Plymouth, MN (US)

( * ) Notice: Subject to any disclaimer, the term of this patent is extended or adjusted under 35 U.S.C. 154(b) by 376 days.

(21) Appl. No.: 11/671,725

(22) Filed: Feb. 6, 2007

Related U.S. Application Data

(60) Provisional application No. 60/837,541, filed on Aug. 14, 2006.

(51) Int. Cl.
*F25D 3/08* (2006.01)

(52) U.S. Cl. .......................... 62/371; 62/457.1; 62/530

(58) Field of Classification Search .................. 62/371, 62/457.1, 457.2, 457.7, 530
See application file for complete search history.

(56) References Cited

U.S. PATENT DOCUMENTS

| | | | |
|---|---|---|---|
| 3,077,426 A | 2/1963 | Johnston | |
| 3,262,283 A * | 7/1966 | Taylor .......................... | 62/372 |
| 3,786,613 A | 1/1974 | Shepheard | |
| 3,810,367 A | 5/1974 | Peterson | |
| 4,044,449 A | 8/1977 | Phan | |
| 4,145,895 A | 3/1979 | Hjertstrand et al. | |
| 4,147,004 A | 4/1979 | Day et al. | |
| 4,527,370 A | 7/1985 | Schuette | |
| 4,923,077 A | 5/1990 | Van Iperen et al. | |
| 5,050,387 A | 9/1991 | Bruce | |
| 5,093,175 A | 3/1992 | Goto et al. | |
| 5,758,513 A | 6/1998 | Smith | |
| 5,848,508 A | 12/1998 | Albrecht | |
| 5,875,599 A | 3/1999 | McGrath et al. | |
| 5,899,088 A | 5/1999 | Purdum | |
| 5,924,302 A | 7/1999 | Derifield | |
| 6,164,030 A | 12/2000 | Dietrich | |
| 6,209,343 B1 | 4/2001 | Owen | |
| 6,223,551 B1 | 5/2001 | Mitchell | |
| 6,233,965 B1 | 5/2001 | Choy | |
| 6,266,972 B1 | 7/2001 | Bostic | |
| 6,502,417 B2 | 1/2003 | Gano, III | |
| 6,658,857 B1 | 12/2003 | George | |
| 6,718,776 B2 | 4/2004 | Wessling et al. | |
| 2002/0144482 A1 | 10/2002 | Henson et al. | |
| 2004/0025528 A1 * | 2/2004 | Gano, III ...................... | 62/371 |
| 2004/0074208 A1 | 4/2004 | Olson et al. | |
| 2004/0180176 A1 | 9/2004 | Rusek, Jr. | |

FOREIGN PATENT DOCUMENTS

DE 10305550 A1 8/2004

* cited by examiner

*Primary Examiner*—Melvin Jones
(74) *Attorney, Agent, or Firm*—Elizabeth D. Lewen; Sherrill Law Offices, PLLC

(57) ABSTRACT

An apparatus having a plurality of phase change material-containing wall panels. The wall panels have a thickness and sides. The wall panels define an inner major surface and an outer major surface. The sides of the wall panels are hingedly interconnected to define a closed structure. Two diametrically opposed hinge interconnections are proximate the inner major surface. The remaining hinge interconnections are proximate the outer major surface.

5 Claims, 3 Drawing Sheets

COLLAPSIBLE INTERCONNECTED PANELS OF PHASE CHANGE MATERIAL

This application claims the benefit of U.S. Provisional Application No. 60/837,541, filed Aug. 14, 2006.

BACKGROUND

Medical supplies such as blood, medicine, and vaccines often need to be maintained within a given temperature range. Transport is particularly challenging. The currently accepted method of transporting blood is to place the blood in a reusable cardboard box lined with expanded polystyrene, called a "Collins Box." The liquid blood products are covered with 14 pounds or more of cubed, wet ice which is double bagged and secured with electrical tie-down straps to maintain temperatures of 1° to 10° C. within the box.

Using a Collins Box requires the need to procure and store at least 14 pounds of cubed wet ice for each box. For large shipments of blood requiring multiple Collins Boxes, significant amounts of storage space is needed for the cubed ice. Using ice also allows for highly non-uniform temperatures within the container.

There have been some attempts to replace the ice in Collins boxes using phase change material containing panels. Examples can be found in U.S. Patent Application Publication US 2004/0079793 A1, U.S. Pat. No. 4,923,077 and U.S. Pat. No. 6,502,417 B2. The past attempts at using phase change material containing panels are complicated to properly assembly for use and leave gaps between panels that can affect the uniform temperature in the inner chamber.

Therefore, a need exists for a blood transportation system that requires less storage space for components needed for use, is easy and uncomplicated to assemble, and provides a more uniform temperature within the inner chamber during transport.

SUMMARY OF THE INVENTION

The invention is an apparatus having a plurality of phase change material-containing wall panels. The wall panels have a thickness and sides. The wall panels define an inner major surface and an outer major surface. The sides of the wall panels are hingedly interconnected to define a closed structure. Two diametrically opposed hinge interconnections are proximate the inner major surface. The remaining hinge interconnections are proximate the outer major surface.

DETAILED DESCRIPTION OF A PREFERRED EMBODIMENT

Definitions

As utilized herein, including the outline of the invention, the term "polygon" refers to a closed plane figure bounded by straight lines.

Nomenclature

10 Apparatus
20 Panel
20t Thickness
20r Right side of panel
20s Left side of panel
20a Inner major surface
20b Outer major surface
21 Wall Panel
22 Top Panel
23 Bottom Panel
30 Hinge

Construction

Figure 1:
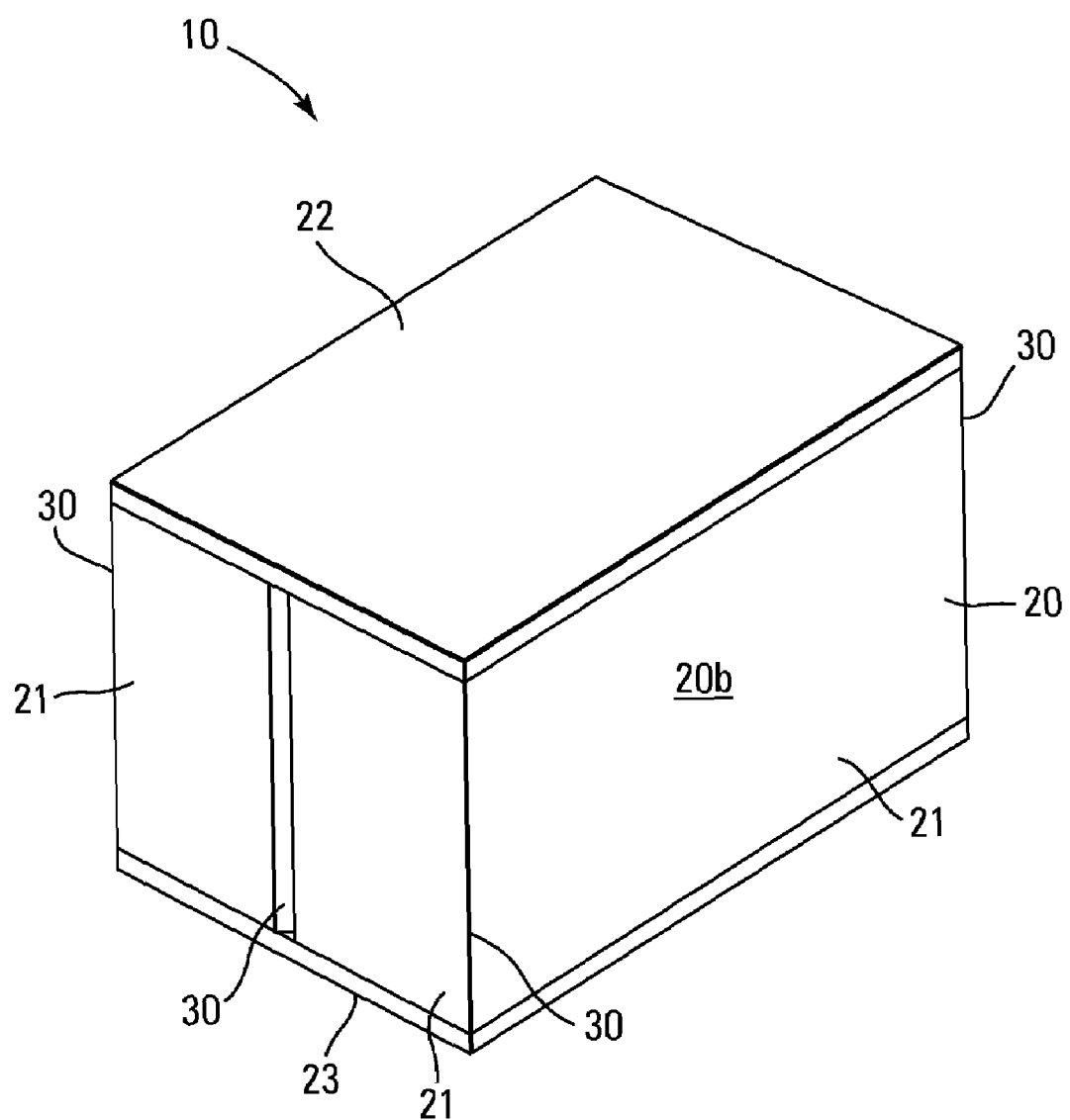
FIG. 1 is a perspective view of one embodiment of the apparatus with top and bottom panels.
Figure 2:
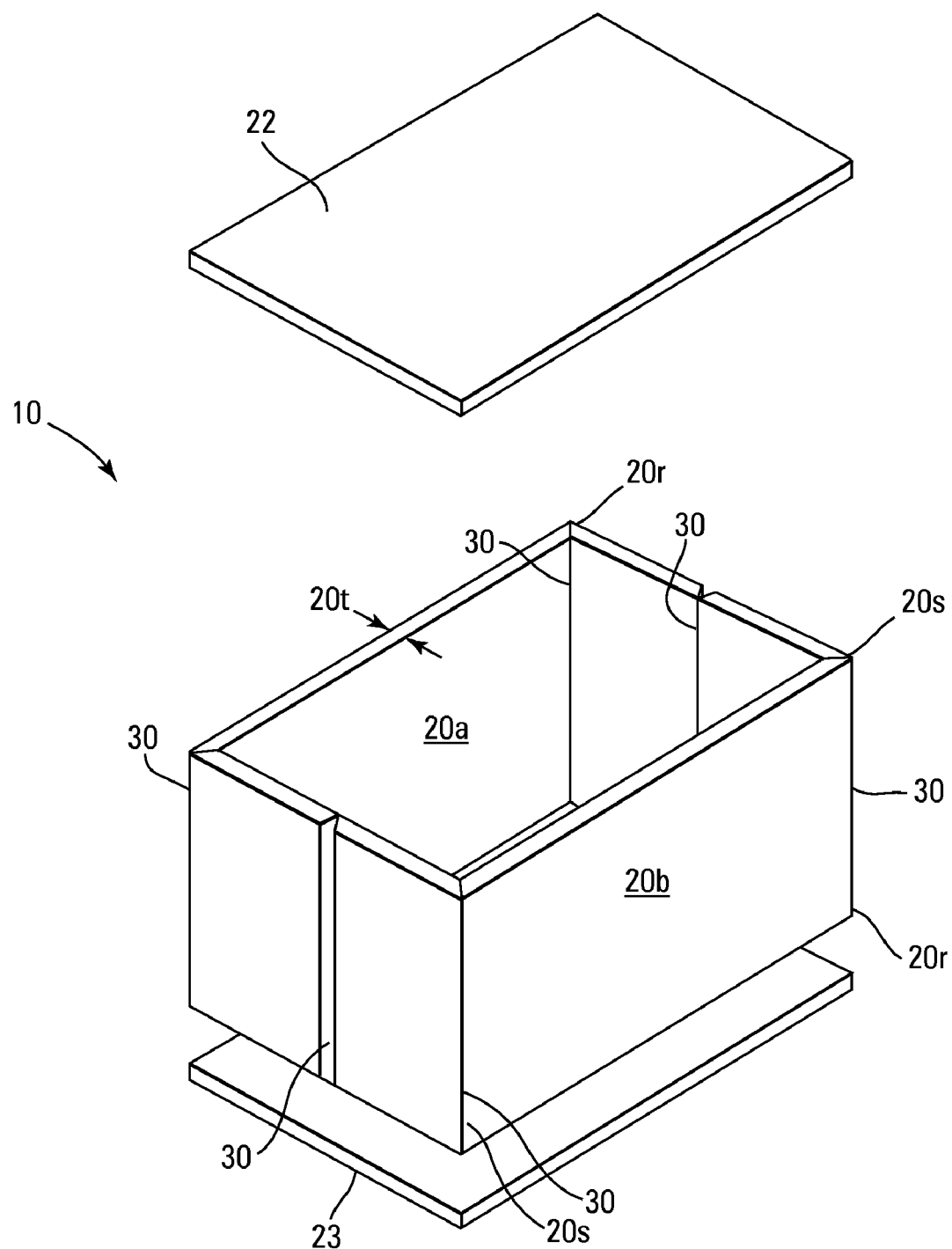
FIG. 2 is an exploded view of the apparatus as shown in FIG. 1.

As shown in FIGS. 1 and 2, one embodiment of the apparatus 10 comprises a plurality of phase change material containing panels 20. The panels 20 have at least a thickness 20t and a right side 20r and a left side 20s. The plurality of panels 20 defines an inner major surface 20a and an outer major surface 20b. The thickness 20t of the panels 20 may be any suitable thickness 20t allowing the desired amount of phase change material to be contained in the panels 20.

The apparatus 10 may contain any number of wall panels 21. Preferably the apparatus 10 has at least three wall panels 21 and most preferably six wall panels 21. The left sides 20s and right sides 20r of the wall panels 21 are hingedly interconnected to define a closed structure (not numbered). The hinge 30 interconnection may allow the apparatus 10 to define a closed structure with a variety of polygon perimeter shapes. The preferred perimeter shape of the closed structure is a rectangle. Preferably the wall panels 21 are rigid to help maintain the desired shape of the apparatus 10 and the defined closed structure. The preferred method of manufacture of the wall panels 21 is by twin sheet pressure forming.

The number of hinge 30 interconnections may be directly proportional to the number of wall panels 21. Each hinge 30 interconnection may be one or more hinges 30 connecting two wall panels 21. As shown in FIGS. 1 and 2, preferably each hinge 30 interconnection is one hinge 30 substantially spanning the entire length (not numbered) of the left side 20s and right side 20r of the wall panels 21 being interconnected. Most preferably all but one hinge 30 interconnection are living hinges 30. Wherein the living hinges 30 substantially span the entire length of the left side 20s and right side 20r of the wall panels 21 being interconnected. The remaining hinge 30 may be a non-integral hinge 30 substantially spanning the entire length of the left side 20s and right side 20r of the wall panels 21 being interconnected. This may help to maintain a more uniform temperature within the closed structure.

Figure 3:
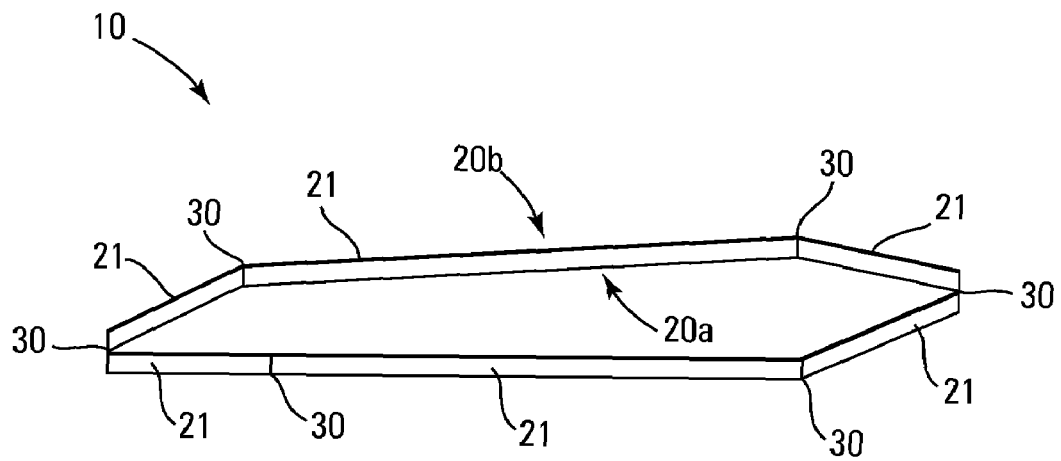
FIG. 3 is a top view of the apparatus as shown in FIG. 1, partially collapsed.
Figure 4:
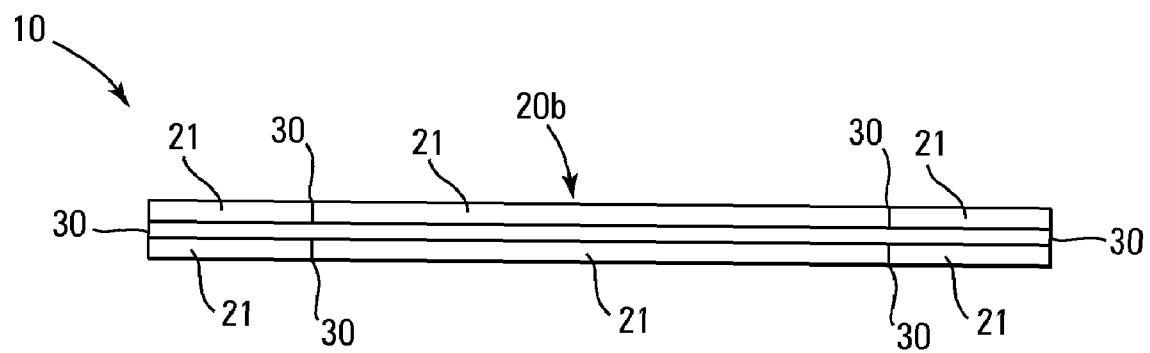
FIG. 4 is a top view of the apparatus as shown in FIG. 1, completely collapsed.

At least two diametrically opposed hinge 30 interconnections are proximate the inner major surface 20a of the apparatus 10. The remainder of the hinge 30 interconnections may be proximate the outer major surface 20b of the apparatus 10. As shown in FIGS. 3 and 4, placing two diametrically opposed hinge 30 interconnections proximate the inner major surface 20a may allow the wall panels 21 to be collapsible to form a more compact structure for ease of storage and ease of placement in a freezer or refrigerator (not shown) for cooling of the phase change material.

Use

As shown in FIG. 4, the apparatus 10 may be stored in a collapsed position for storage. When the apparatus 10 is needed to provide a controlled temperature environment, the apparatus 10 may be subjected to an environment allowing the phase change material to reach the desired state and temperature. The collapsibility of the apparatus 10 allows more than one apparatus 10 to be stacked together to utilize space not only in storage but also during freezing or refrigeration of the phase change material if needed.

Once the apparatus 10 is ready for use it may be inserted into another container such as a cooler, a shipping or packing box or other suitable container having an insulation layer and a protective layer as disclosed in U.S. Patent Application Publication 2004/0079793 and U.S. Pat. No. 4,923,077. The apparatus 10 may be easily manipulated to conform to the perimeter shape of the container by manipulating the apparatus 10 about the hinge 30 interconnections. The hinge 30 interconnections proximate the outer major surface 20b of the apparatus 10 may allow the thickness 20t of the wall panels 21 proximate the hinges 30 to lie against one another and prevent the hinge 30 from completely closing and maintaining the desired shape of the closed structure. If a top panel 22 or bottom panel 23 is to be used with the apparatus 10, the bottom panel 23 may be inserted into the container prior to inserting the apparatus 10. The top panel 22 is then set upon the apparatus 10.

Once the use of the apparatus 10 is complete, the apparatus 10 may be removed from the container and collapsed for storage or again subjected to an environment allowing the phase change material to reach the desired state and temperature for use again. The apparatus 10 may be collapsed by manipulating the wall panels 21 as shown in FIGS. 3 and 4 to open the hinges 30 proximate the outer major surface 20b and closing the hinges 30 proximate the inner major surface 20a.

I claim:

1. An apparatus, comprising a plurality of phase change material-containing wall panels having a thickness and sides, each shaped as a frustum of a wedge and each defining an inner major surface and an outer major surface wherein (i) the sides of the wall panels are hingedly interconnected, and (ii) two diametrically opposed hinge interconnections are proximate the inner major surface and a remaining hinge interconnections are proximate the outer major surface.

2. The apparatus, as recited in claim 1, further comprising a top panel and a bottom panel.

3. A collapsible enclosure, comprising a plurality of phase change material-containing panels each having a thickness, a top edge, a bottom edge, and side edges, each shaped as a frustum of a wedge, and each defining an inner major surface and an outer major surface wherein the sides of each panel are each hingedly interconnected to the side of an adjacent panel so as to define a continuous encircling band of hingedly interconnected panels.

4. A collapsible enclosure, comprising a plurality of phase change material-containing panels having a thickness and sides, and defining an inner major surface and an outer major surface wherein (i) the sides of the panels are hingedly interconnected to define a closed structure, and the closed structure is collapsible wherein the inner major surface of one panel will overlay the inner major surface of a diametrically opposed panel.

5. The apparatus, as recited in claim 4, wherein the wall panels are shaped as a frustum of a wedge.

* * * * *